US008815222B2

(12) United States Patent  
Pan et al.

(10) Patent No.: US 8,815,222 B2
(45) Date of Patent: *Aug. 26, 2014

(54) ANHYDROUS LIQUID ANTIPERSPIRANT COMPOSITION

(75) Inventors: Long Pan, Cherry Hill, NJ (US); Donghui Wu, Bridgewater, NJ (US); LaTonya Kilpatrick-Liverman, Princeton, NJ (US); Matthew J. Eibling, Convent Station, NJ (US); Michael Fitzgerald, Oakhurst, NJ (US); Iraklis Pappas, Pennsauken, NJ (US)

(73) Assignee: Colgate—Palmolive Company, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/518,941

(22) PCT Filed: Dec. 16, 2010

(86) PCT No.: PCT/US2010/060634
§ 371 (c)(1),
(2), (4) Date: Jun. 25, 2012

(87) PCT Pub. No.: WO2011/079001
PCT Pub. Date: Jun. 30, 2011

(65) Prior Publication Data
US 2012/0282205 A1    Nov. 8, 2012

Related U.S. Application Data

(60) Provisional application No. 61/289,433, filed on Dec. 23, 2009.

(51) Int. Cl.
| *A61Q 15/00* | (2006.01) |
| *A61K 8/00* | (2006.01) |
| *A61K 8/26* | (2006.01) |
| *A61K 8/44* | (2006.01) |
| *A61K 8/42* | (2006.01) |

(52) U.S. Cl.
CPC ... *A61K 8/44* (2013.01); *A61K 8/42* (2013.01); *A61K 8/26* (2013.01); *A61Q 15/00* (2013.01); *A61K 2800/58* (2013.01); *A61K 2800/31* (2013.01)
USPC .............................. 424/65; 424/68

(58) Field of Classification Search
CPC .......... A61Q 15/00; A61K 8/44; A61K 8/26; A61K 8/42; A61K 2800/58; A61K 2800/31
USPC ..................................... 424/65, 68
See application file for complete search history.

(56) References Cited

U.S. PATENT DOCUMENTS

| 2,230,082 | A | 1/1941 | Montenier |
| 2,236,387 | A | 3/1941 | Wallace et al. |
| 3,928,557 | A | 12/1975 | Wright et al. |
| 3,932,609 | A | 1/1976 | Rosenstreich et al. |
| 3,981,986 | A | 9/1976 | Rubino |
| 4,069,299 | A | 1/1978 | Hodgson |
| 4,113,852 | A | 9/1978 | Kenkare et al. |
| 4,777,034 | A | 10/1988 | Olivier et al. |
| 5,179,220 | A * | 1/1993 | Katsoulis et al. ............... 556/27 |
| 5,676,936 | A | 10/1997 | Park |
| 6,007,799 | A | 12/1999 | Lee et al. |
| 6,375,937 | B1 | 4/2002 | Chopra et al. |
| 6,960,338 | B2 | 11/2005 | Li et al. |
| 7,074,394 | B2 | 7/2006 | Li et al. |
| 7,105,691 | B2 | 9/2006 | Holerca et al. |
| 7,183,433 | B2 * | 2/2007 | Abbott et al. ................. 564/282 |
| 7,303,743 | B2 | 12/2007 | Hurley et al. |
| 2003/0044368 | A1 | 3/2003 | Tsuchikura |
| 2004/0028614 | A1 * | 2/2004 | Corbella et al. ............... 424/45 |
| 2004/0077519 | A1 | 4/2004 | Price et al. |
| 2004/0097755 | A1 | 5/2004 | Abbott et al. |
| 2004/0109833 | A1 | 6/2004 | Tang et al. |
| 2004/0198998 | A1 | 10/2004 | Holerca et al. |
| 2004/0265255 | A1 * | 12/2004 | Holerca et al. ................. 424/66 |
| 2006/0094620 | A1 | 5/2006 | Jordan et al. |
| 2006/0094621 | A1 | 5/2006 | Jordan et al. |
| 2006/0204463 | A1 | 9/2006 | Tang et al. |
| 2006/0240728 | A1 * | 10/2006 | Price et al. ..................... 442/59 |
| 2007/0110687 | A1 | 5/2007 | Mattai et al. |
| 2007/0196308 | A1 | 8/2007 | Popoff et al. |
| 2008/0070966 | A1 | 3/2008 | Elder et al. |
| 2009/0257970 | A1 | 10/2009 | Bloom |

FOREIGN PATENT DOCUMENTS

| CA | 2257559 | 12/1997 |
| DE | 102005026355 | 12/2006 |
| EP | 0281812 | 9/1988 |
| EP | 0914138 | 5/1999 |

(Continued)

OTHER PUBLICATIONS

Nockemann et al., Journal of Physical Chemistry, 110: 20978-20992 (2006).*
Abbott et al., 2003, "Novel Solvent Properties of Choline Chloride/Urea Mixtures", Chemical Communications 2003(1):70-71.
Abbott et al., 2004, "Deep Eutectic Solvents Formed between Choline Chloride and Carboxylic Acids: Versatile Alternatives to Ionic Liquids", Journal of The American Chemical Society 126:9142-9147.

(Continued)

*Primary Examiner* — Daniel Sullivan
*Assistant Examiner* — Lisbeth C Robinson
(74) *Attorney, Agent, or Firm* — Michael F. Morgan

(57) ABSTRACT

An anhydrous liquid antiperspirant/deodorant composition comprising a carrier comprising a cation and/or zwitterion and a hydrogen bond donor, wherein an amount of carrier is greater than an amount of any other material in the composition, and an antiperspirant active. This represents a new delivery form for antiperspirant actives and/or deodorant actives.

16 Claims, No Drawings

(56) References Cited

FOREIGN PATENT DOCUMENTS

| GB | 2076289 A | * 12/1981 |
|---|---|---|
| WO | WO 2006/091417 | 8/2000 |
| WO | WO 2007/059530 | 5/2007 |
| WO | WO 2007/064756 | 6/2007 |
| WO | WO 2011/087701 | 7/2011 |
| WO | WO 2011/087702 | 7/2011 |

OTHER PUBLICATIONS

Binnemans, 2005, "Ionic Liquid Crystals", Chemical Reviews 105:4148-4204.
Binnemans, 2007, "Lanthanides and Actinides in Ionic Liquids", Chemical Reviews 107:2592-2614.
Chi et al., 1998, "Preventing Discoloration of Squalene-soiled Cotton Fabrics with Antioxidants", Journal of Surfactants and Detergents 1(4):523-527.
Coehlo-Sampaio et al., 1994, "Betaine Counteracts Urea-induced Conformational Changes and Uncoupling of the Human Erythrocyte $Ca^{2+}$Pump", European Journal of Biochemistry 221:1103-1110.
Davis et al., 2003, "Town Curiosities to Conmodities: Ionic Liquids Begin the Transition", Chemical Communications 11:1209-1212.
Dupont et al., 2002, "Ionic Liquid (Molten Salt) Phase Organometallic Catalysis", Chem. Rev. 102:3667-3692.
Endres et al., 2006, "Air and Water Stable Ionic Liquids in Physical Chemistry", Physical Chemistry Chemical Physics 8:2101-2116.
FDA, 1978, Monograph on Antiperspirant Dry Products, Oct. 10, 1978.
Feng et al., 2007, "Speciation of Hydroxyl-Al Polymers Formed through Simultaneous Hydrolysis of Aluminum Salts and Urea", Colloids & Surfaces A 303:241-248.
Greaves et al., 2008, "Protic Ionic Liquids: Properties and Applications", Chemical Reviews 108:206-237.
Hardacre et al., 2007, "Structure and Solvation in Ionic Liquids", Accounts of Chemical Research 40:1146-1155.
Holzle et al., 1984, "Structural Changes in Axillary Eccrine Glands Following Long-term Treatment with Aluminium Chloride Hexahydrate Solution", British Journal of Dermatology 110:399-403.
Huddleston et al., 2001, "Characterization and Comparison of Hydrophilic and Hydrophobic Room Temperature Ionic Liquids Incorporating the Imidazolium Cation", Green Chemistry 3:156-164.
Morrison, et al., 2009, Characterization of Thermal Behavior of Deep Eutectic Solvents and Their Potential as Drug Solubilization Vehicles, International Journal of Pharmacy 378:136-139.
Nockemann et al., 2006, "Task-Specific Ionic Liquid for Solubilizing Metal Oxides", Journal of Physical Chemistry B 110:20978-20992.
Padua et al., 2007, "Molecular Solutes in Ionic Liquids: A Structural Perspective", Accounts of Chemical Research 40:1087-1096.
Parnham et al., 2007, "Ionothermal Synthesis of Zeolites, Metal-Organic Frameworks, and Inorganic-Organic Hybrids", Accounts of Chemical Research 40:1005-1013.
Parvulesca et al., 2007, "Catalysis in Ionic Liquids", Chemical Reviews 107:2615-2665.
PCT/US2010/060630—ISR and Written Opinion mailed May 25, 2012.
PCT/US2010/060633—ISR and Written Opinion mailed May 24, 2012.
PCT/US2010/060634—ISR and Written Opinion mailed May 25, 2012.
Plechkova et al., 2008, "Applications of Ionic Liquids in the Chemical Industry", Clemical Society Reviews 37:123-150.
Ranke et al., 2007, "Design of Sustainable Chemical Products—The Example of Ionic Liquids", Chemical Reviews 107:2183-2206.
Rantwijk et al., 2007, "Biocatalysts in Ionic Liquids", Chemical Reviews 107:2757-2785.
Rogers et al., 2007, "Ionic Liquids", Accounts of Chemical Research 40(11):1077-1078.
RSC, 2005, "Salty Solvents—Ionic Really", Royal Society of Chemicals.
Schaber et al., 2004, "Thermal Decomposition (pyrolysis) of Urea in an Open Reaction Vessel", Thermochimicta Acta 424:131-142.
Shafran et al., 2004. "High Temperature Speciation Studies of Al-Ion Hydrolysis", Advanced Enigineering Materials 6(10):836-839.
Shaw et al., 1955, "The Decomposition of Urea in Aqueous Media", Journal of the American Chemistry Society 77(18)4729-4733.
Short, 2006, "Out of the Ivory Tower: Ionic Liquids Are Starting to Leave Academic Labs and Find Their Way into a Wide Variety of Industrial Applications", Chemical & Engineering News 84-(17):15-21.
Smiglak et al., 2007, "The Second Evolution of Ionic Liquids: From Solvents and Separations to Advanced Materials—Energetic Examples from the Ionic Liquid Cookbook", Accounts of Chemical Research 40: 1182-1192.
Vogels et al., 2005, "Honogenious Forced Hydrolysis of Aluminum Through the Thermal Decomposition of Urea", Journal of Colloid and Interface Science 285:86-93.
Wang et al., 2006. "A Theoretical Investigation of the Interactions between Water Molecules and Ionic Liquids", Journal of Physical Chemistry B 110:24646-24651.
Welton, 1999, "Room-Temperature Ionic Liquids. Solvents for Synthesis and Catalysts", Chemical Reviews 99:2071-2083.
Wikipedia entry, 2004. "Ionic Liquid".
Wikipedia entry, 2005, "Deep Eutectic Solvent".
Yancey et al., 1982, "Living with Water Stress: Evolution of Osmolyte Systems", Science. 217:1214-1222.

* cited by examiner

ANHYDROUS LIQUID ANTIPERSPIRANT COMPOSITION

CROSS REFERENCE TO RELATED APPLICATIONS

This application is a national stage entry under 35 U.S.C. §371 of International Patent Application No. PCT/US2010/060634, filed 16 Dec. 2010, which claims priority to U.S. Provisional Patent Application Ser. No. 61/289,433, filed on 23 Dec. 2009, which are incorporated herein by reference.

BACKGROUND

There have been several forms of antiperspirant/deodorant products, such as sticks, soft solids, roll-ons, and aerosols. The different fauns deliver antiperspirant and/or deodorant actives to axillary areas. There can be disadvantages when formulating these type of products.

One disadvantage is that when an antiperspirant active is included, steps need to be taken to stabilize the antiperspirant from hydrolyzing and polymerizing during storage. When an antiperspirant polymerizes into larger species, the efficacy is reduced.

Another disadvantage is that materials used for delivery, such as in the sticks or soft solids, can leave a white residue on the skin. This can be aesthetically unpleasing when seen on skin or when transferred to clothing during wearing.

It would be advantageous to develop a new form of delivery of antiperspirant and/or deodorant actives.

SUMMARY

An anhydrous liquid antiperspirant/deodorant composition comprising:
a) a carrier comprising i) at least one member chosen from a cation and zwitterion and ii) a hydrogen bond donor, wherein an amount of carrier is greater than an amount of any other material in the composition, and
b) at least one active chosen from an antiperspirant active and a deodorant active.

DETAILED DESCRIPTION

As used throughout, ranges are used as a shorthand for describing each and every value that is within the range. Any value within the range can be selected as the terminus of the range. In addition, all references cited herein are hereby incorporated by reference in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material unless otherwise specified.

By anhydrous it is meant that the composition contains 5 weight % or less free water. In other embodiments, the maximum amount of water is 4, 3, 2, or 1 weight %. In one embodiment, the maximum amount of water is 2 weight %. In certain embodiments, there is no free water. When calculating the water, water molecules that are part of a hydrate of a material are not counted. Too much water in the composition can hydrolyze the antiperspirant active to polymerize it, which reduces it effectiveness.

In one embodiment, the composition is a liquid at 0° C. to 100° C. In one embodiment, the composition is a liquid at 100° C. or below. In another embodiment, the composition is a liquid at 30° C. or below.

The liquid anhydrous antiperspirant/deodorant composition comprises a carrier that is a mixture of i) a cation and/or zwitterion and ii) a hydrogen bond donor. The term cation/zwitterion refers to a selection of at least one of the cation and zwitterion. Either one or both can be present. The carrier is present in an amount that is more than any other single material in the composition. In certain embodiments, the carrier is at least 50 weight % of the composition. In other embodiments, the carrier is at least 55, 60, 65, 70, 75, 80, 85, or 90 weight % of the composition. The mixture of i) a cation and/or zwitterion and ii) a hydrogen bond donor is the majority of the carrier.

The combination of the cation/zwitterion and the hydrogen bond donor can form a deep eutectic solvent. A deep eutectic solvent is a mixture that forms a eutectic with a melting point lower than either of the individual components.

Examples of the cation/zwitterion include, but are not limited to, quaternary ammonium salts, trimethylglycine, trimethylglycine hydrochloride, amino acids, glycine, and choline chloride. In one embodiment, the cation/zwitterion comprises trimethylglycine and glycine. In one embodiment, the amount of cation/zwitterion is 30 to 50 weight % of the composition. In other embodiments, the amount is at least 35, 40, or 45 up to 50 weight % or no more than 45, 40, or 35 down to 30 weight % of the composition.

Betaine in IUPAC nomenclature is 1-carboxy-N,N,N-trimethylmethanaminium hydroxide-inner salt, with alternative names including carboxymethyl-trimethyl-ammonium betaine or (carboxymethyl)trimethylammonium hydroxide-inner salt or glycine betaine or glycol betaine or glycyl betaine or trimethylglycine or trimethylglycol. Betaine is not to be confused with betaine surfactants.

Examples of the hydrogen bond donor include, but are not limited to, urea. Generally, the hydrogen bond donor can be any hydrogen bond donor that can be included in personal care products. In one embodiment, the amount of hydrogen bond donor is 30 to 45 weight % of the composition. In other embodiments, the amount is at least 35 or 40 up to 45 weight % or no more than 40 or 35 down to 30 weight % of the composition.

In one embodiment, the carrier is a mixture of trimethylglycine and urea. In certain embodiments, the molar ratio of trimethylglycine to urea is 4:6 to 1:9. In one embodiment, the molar ratio of trimethylglycine to urea is 1:2. In other words, the carrier is 60 to 90 molar % urea, and in one embodiment, it is 67 molar %.

When urea is used to neutralize aluminum chloride, and trimethylglycine provides an additional benefit as a buffer along with sodium chloride, a liquid state antiperspirant composition is obtained that is mainly composed of the smaller aluminum species, which can be demonstrated by standard Size Exclusion Chromatograph (SEC). The SEC spectra of this liquid state antiperspirant composition is dominated by "peak 4", which is the smaller aluminum species that are known to have very good antiperspirant efficacy.

In certain variations of the carrier comprising the trimethylglycine and urea embodiment, a portion of the urea can be replaced by other hydrogen bond donors. In one embodiment, 20-50 molar % of the urea can be replaced.

Antiperspirant actives include, but are not limited to, aluminum chloride, aluminum chlorohydrate, aluminum sesquichlorohydrate, aluminum-zirconium hydroxychlorides, complexes or adducts of the above-mentioned active ingredients with glycol, such as propylene glycol (for example, "Rehydrol" II from SummitReheis), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products for overall-the-counter human use (Oct. 10, 1973) can be used. Specific examples of commercialized aluminum-zirconium salts include AZP-908 and Z-576 from SummitReheis (Huguenot, N.Y.).

In other embodiments, the antiperspirant active is an aluminum salt and/or an aluminum-zirconium salt, such as those described above, that are further stabilized by trimethylglycine and a calcium salt. More information about betaine and calcium salt stabilized antiperspirant salts can be found in U.S. Patent Application Publication No. 2006/0204463 to Tang et al.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al., which are incorporated herein by reference only for their disclosure of the antiperspirant active.

In other embodiments, the type of salt of interest, an aluminum zirconium tetrasalt or octasalt free of glycine are used wherein aluminum zirconium salt is stabilized by betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the betaine:zirconium mole ratio can be about 0.2:1 to about 3.0:1 (or in other embodiments of about 0.4:1 to about 1.5:1). Another salt that can be used is an aluminum chloride salt buffered by betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the betaine:Zr mole ratio is about 0.2:1 to about 3.0:1 (or in other embodiments of about 0.4:1 to about 1.5:1). In one embodiment, in the case of a salt that contains zirconium, the betaine is incorporated during the synthesis of the salt so as to maximize the stabilizing effect this ingredient has (especially on the zirconium species). Alternatively, it can be post added to a glycine-free salt along with additional active phase ingredients to form a betaine stabilized active.

Examples of commercially available glycine-free low M:Cl ratio tetrasalts and octasalts include, but are not limited to, REZAL™ AZP 955 CPG and REZAL™ AZP 885 respectively (both from SummitReheis Chemical Company, Huguenot, N.Y.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

Additionally, the antiperspirant active can be a calcium salt stabilized antiperspirant active. Examples of calcium salt stabilized antiperspirant actives can be found in U.S. Patent Application Publication No. 2006/0204463, which is incorporated herein by reference only for the disclosure of the calcium salt stabilized antiperspirant actives.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorohydrex propylene glycol, aluminum zirconium trichlorohydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorohydrate. In another embodiment, the antiperspirant active is aluminum zirconium tetrachlorohydrex propylene glycol.

The amount of antiperspirant active can be any of the regulatory allowed amounts for each type of antiperspirant active. In certain embodiments, the amount is up to 25 weight % for an over the counter composition. In certain embodiments, the amount is 5 to 25 weight % of the composition. In other embodiments, the amount is at least 5, 10, or 15 up to 20 weight % of the composition.

Aluminum chloride refers to the hydrate focus. In one embodiment, the hydrate form comprises $AlCl_3 \cdot 6H_2O$. In one embodiment, the amount of aluminum chloride is up to 20 weight %. In other embodiments, the amount is up to 18, 17, 16, 15, 14, 13, 12, 11, 10, 9, 8, 7, 6, or 5 weight %.

Examples of deodorant actives include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammomium bromide, cetyl pyridinium chloride, farnesol (3,7,11-trimethyl-2,6,10-dodecatrien-1-ol), bactericides, and/or bacteriostats. In certain embodiments, the amount of deodorant actives is 1 to 20 weight % of the composition.

A stabilizing agent can optionally be included in the composition. The stabilizing agent is any material that is present in an amount such that the composition is liquid below 100° C. The amount of stabilizing agent varies by the stabilizing capability of each stabilizing agent. In certain embodiments, the amount of stabilizing agent is 1 to 20 weight % of the composition. In other embodiments, the amount of stabilizing agent is at least 1, 2, 3, 4, 5, 6, 7, 8, 9, or 10 up to 20 weight % of the composition. In other embodiments, the amount is less than 20, 15, 10, 9, 8, 7, 6, 5, 4, 3, or 2 down to 1 weight % of the composition. Examples of stabilizing agents include, but are not limited to, PPG-14 butyl ether, chloride salts, sodium chloride (NaCl), potassium chloride, bromides, nitrates, organic acids, glycerin, alcohol, ethanol, and isopropanol.

In certain embodiments, the anhydrous liquid antiperspirant/deodorant composition can be extremely viscous, and its skin-feel can be described as a mixture of greasy, sticky, and tacky. To improve the skin feel of the composition, skin-feel additives can be added. In one embodiment, the amount of skin-feel additives is 1 to 8 weight % of the composition. In other embodiments, the amount is at least 1, 2, 3, 4, or 5 up to 8 weight %. In other embodiments, the amount is less than 8, 7, 6, 5, 4, 3, or 2 down to 1 weight %. In certain embodiments, the amount of skin-feel additives is up to 10 weight % to allow for more delivery of the antiperspirant active.

The optional skin-feel additives that can be used include, but are not limited to, water, isopropanol, ethanol, cocamidopropyl betaine, cyclomethicone (such as DC345), PEG-12 dimethicone copolyol (DC5329), steareth-2/steareth-20, polyoxyethylene homopolymer (POLYOX™ WSR-N 750 from Dow Chemical), palm kernel oil, mineral oil, and silicone polyether wax (Silwax from Siltech).

Water: It is one of the easiest additives to combine with the anhydrous liquid antiperspirant/deodorant composition, and even in small amounts it can improve viscosity. Because aluminum hydrolysis becomes an issue with increasing availability of water, the amount of added water in the examples below has been capped at 2 weight %. Although there is an improvement in the "spreadability" of anhydrous liquid antiperspirant/deodorant composition when 2 weight % water is added, its tendency to bead increases and it forms large pools on the skin surface. This effect can be unappealing. The benefit is that the formula remains clear.

Isopropanol (70%): Because it is 30% water, only 6.7 weight % or less is combined with anhydrous liquid antiperspirant composition to keep additional water at 2 weight % or below. The alcohol will disperse in anhydrous liquid antiperspirant/deodorant composition with vigorous shaking and remain dispersed for a limited time due to the emulsifying effect of water in the system. The dispersion will break after about an hour, and the alcohol will layer on top of the anhydrous liquid antiperspirant composition. A 6.7 weight % formulation is less viscous than the original anhydrous liquid antiperspirant/deodorant composition and forms a white, opaque, lotion-like product. It is of a low enough viscosity to be applied via pump spray. When the minimum is applied (0.06-0.08 g/60-80 cm$^2$), it is easily spread across the skin and feels like petroleum jelly but less viscous. Beading is greatly reduced and is almost imperceptible. A satin sheen is left on the skin. Comments on the formulation describe an initial greasiness that fades with further spreading. The dispersion can be stabilized with 0.1-2 weight % cocamidopropyl betaine.

Isopropanol Alcohol (100%): Because there is no water, this can be added in whatever amount desired, however, total additives are typically capped at 10 weight % to maintain an anhydrous liquid antiperspirant/deodorant composition potency of 90 weight % or greater. Addition of this has a noticeable effect on viscosity but not as much as 70% isopropanol. A 10 weight % formulation will form a rough dispersion (large droplets of isproanol in anhydrous liquid antiperspirant composition), but will still spread nicely on the skin, and it is easily dispensed with a pump spray. The dispersion breaks in less than an hour (sometimes in minutes), and the product needs to be mixed between applications. Formulations with 100% isopropanol "dry" more quickly than those with 70%, and a thinner film is often achieved.

Ethanol (100%): It is similar in action to 100% isopropanol, but it is slightly more soluble in the anhydrous liquid antiperspirant/deodorant composition. Also, most formulations with ethanol remain clear. Anhydrous liquid antiperspirant composition formulations with greater than 15 weight % ethanol have a viscosity and skin-feel close to that of current roll on products, but have an anhydrous liquid antiperspirant/deodorant composition potency less than 85 weight %.

Cocamidopropyl betaine (CAPB): To retain the benefits of isopropanol-based formulations, an emulsifier can be added to stabilize the dispersion. Cocamidopropyl betaine comes as a 30% solution in water, which limits its total use in an anhydrous liquid antiperspirant composition formulation to no more than 3 weight %. This is not a problem considering effective amounts range from 0.1-2 weight % depending on the amount of isopropanol or other additives. Foaming can occur if the level is too high. Dispersions stabilized with cocamidopropyl betaine are typically semi-opaque white and lotion-like. Cocamidopropyl betaine improves the initial skin-feel of a formulation causing it to feel smoother and less sticky or tacky.

DC345 cyclomethicone from Dow Corning: It is hard to formulate with anhydrous liquid antiperspirant/deodorant composition alone because the two tend to separate, and it causes the anhydrous liquid antiperspirant/deodorant composition to bead even faster than normal. In amounts less than 0.5 weight %, DC345 can reduce tackiness in isopropanol-cocamidopropyl betaine systems without noticeable beading.

DC5329 (PEG-12 Dimethicone Copolyol): It is a silicone-based emulsifier that forms multilamellar vesicles (hydrophilic inside-hydrophobic between bilayers). It stabilizes oil-in-water and silicon-in-water formulations. Its recommended level of use is about 4 weight %. In certain embodiments, it can been used in anhydrous liquid antiperspirant/deodorant compositions at 0.5-2 weight % where it will stabilize but also thicken formulations. 0.5 weight % in an isopropanol formulation will give the product more body but still spread nicely and improve skin adhesion.

Steareth-2/Steareth-20: These two ethoxylated fatty acids can be combined to stabilize an oil-in-water dispersion. They increase viscosity and waxiness in anhydrous liquid antiperspirant/deodorant composition systems. Both are solids at room temp and must be melted together prior to addition, and the anhydrous liquid antiperspirant/deodorant composition must be warm when formulating. The resulting formulation is opaque white and resembles a thick lotion.

Polyox™ WSR-N 750: This is a water soluble resin based on a linear poly(oxyethylene) homopolymer. It will dramatically increase slip and reduce drag during product application. It should be mixed with water before formulation with anhydrous liquid antiperspirant composition. Formulations are based on 0.5 weight % linear poly(oxyethylene) homopolymer (relative to anhydrous liquid antiperspirant composition) that are mixed with as little water as necessary to form a gel. The gel is added to the solid anhydrous liquid antiperspirant composition components and then baked. The gel plasticizes in the molten anhydrous liquid antiperspirant/deodorant composition. The hardened gel is removed, and the anhydrous liquid antiperspirant/deodorant composition with linear poly(oxyethylene) homopolymer is compared to normal anhydrous liquid antiperspirant/deodorant composition. The viscosity is reduced, and skin adhesion is better. It is theorized that the water used to gel the linear poly(oxyethylene) homopolymer migrates into the anhydrous liquid antiperspirant/deodorant composition, which causes the reduction in viscosity, and that only a (0.05 weight % or less w/w in anhydrous liquid antiperspirant/deodorant composition) of the linear poly(oxyethylene) homopolymer actually makes it into the formulation.

The anhydrous liquid antiperspirant/deodorant composition represents a new form of antiperspirant composition. Prior forms included sticks, soft solids, gels, aerosols, and water-based roll-ons. In these prior forms, antiperspirant actives are suspended and undissolved in the compositions. This prevents the formation of transparent compositions. Also, this leads to having white residue when applied to skin, which is undesirable to consumers. The anhydrous liquid antiperspirant/deodorant provides a transparent product with no white residue (compatible to placebo). Also, there is long shelf life, for example up to 10 years can be expected.

The composition can optionally contain emollients in any desired amount to achieve a desired emollient effect. Emollients are known in the art and are used to impart a soothing effect on the skin. Non-volatile emollients are preferable. Classes of non-volatile emollients include non-silicone and silicone emollients. Non-volatile, non-silicone emollients include $C_{12-15}$alkyl benzoate. The non-volatile silicone material can be a polyethersiloxane, polyalkyarylsiloxane or polyethersiloxane copolymer. An illustrative non-volatile silicone material is phenyl trimethicone. Non-limiting examples of emollients can be found in U.S. Pat. No. 6,007,799. Examples include, but are not limited to, PPG-14 butyl ether, PPG-3 myristyl ether, stearyl alcohol, stearic acid, glyceryl monoricinoleate, isobutyl palmitate, glyceryl monostearate, isocetyl stearate, sulphated tallow, oleyl alcohol, propylene glycol, isopropyl laurate, mink oil, sorbitan stearate, cetyl alcohol, hydrogenated castor oil, stearyl stearate, hydrogenated soy glycerides, isopropyl isostearate, hexyl laurate, dimethyl brassylate, decyl oleate, diisopropyl adipate, n-dibutyl sebacate, diisopropyl sebacate, 2-ethyl hexyl palmitate, isononyl isononanoate, isodecyl isononanoate, isotridecyl isononanoate, 2-ethyl hexyl palmitate, 2-ethyl hexyl stearate, Di-(2-ethyl hexyl) adipate), Di-(2-ethyl hexyl) succinate, isopropyl myristate, isopropyl palmitate, isopropyl stearate, octacosanol, butyl stearate, glyceryl monostearate, polyethylene glycols, oleic acid, triethylene glycol, lanolin, castor oil, acetylated lanolin alcohols, acetylated lanolin, petrolatum, isopropyl ester of lanolin, fatty acids, mineral oils, butyl myristate, isostearic acid, palmitic acid, PEG-23 oleyl ether, olelyl oleate, isopropyl linoleate, cetyl lactate, lauryl lactate, myristyl lactate, quaternised hydroxy alkyl, aminogluconate, vegetable oils, isodecyl oleate, isostearyl neopentanoate, myristyl myristate, oleyl ethoxy myristate, diglycol stearate, ethylene glycol monostearate, myristyl stearate, isopropyl lanolate, paraffin waxes, glycyrrhizic acid, hydrocyethyl stearate amide.

The composition can contain a fragrance. Any know fragrance can be used in any desired amount. In one embodiment, the amount of fragrance is 0.01 to 10 weight %.

Antioxidants may be added to the composition, preferably to act as ingredient protectants and for maintenance of long-term stability of the composition. Examples of antioxidants include, but are not limited to butylated hydroxytoluene, pentaerythrityl tetra-di-t-butyl hydroxyhydrocinnamate (Tinogard™ TT from Ciba).

Any of the anhydrous liquid antiperspirant/deodorant compositions can be applied to axillary areas to reduce sweat and/or odor. The compositions can be applied by hand or via their packaging.

SPECIFIC EMBODIMENTS

The invention is further described in the following examples. The examples are merely illustrative and do not in any way limit the scope of the invention as described and claimed.

Synthesis A: Synthesis of a Trimethylglycine/Urea Deep Eutectic Solvent

To a clean 20 mL scintillation vial, add 0.05 mol (5.8551 g) anhydrous trimethylglycine and 0.1 mol (6.0052 g) urea. The mixture is vortexed for 3 minutes and heated at 90° C. for 1 hour. Visual inspection showed that the solid mixture had formed a clear viscous fluid with a few particles of undissolved urea suspended. Agitation and further heating for 2 hours dissolved the suspended particulate. After cooling, the pH was 9.2. The liquid solidified after about 2 hours at room temperature.

The melting point of a trimethylglycine and urea Deep Eutectic liquid was above room temperature (25° C.). Upon cooling to below 30° C., the clear ionic liquid solidified to form a hard, opaque solid with a consistency similar to that of hard wax. Although this solidification process may appear analogous to the freezing of a liquid, there were differences. First, cooling to a very low temperature did not accelerate the solidification. It stabilized the liquid in a clear, amorphous, glass-like state. At room temperature, solidification occurred relatively slowly. Solidification appears to be preceded by the formation of a small ovular bead. Due to the very high viscosity and consequent low ion mobility, it is theorized that this bead may be a seed crystal of either trimethylglycine or urea that forms from a localized concentration build up. After formation of this bead, the liquid begins to solidify in a layered structure.

Synthesis B: Use of PPG-14 Butyl Ether as a Stabilizing Agent for Trimethylglycine/Urea A trimethylglycine/urea DE solvent (DES) is synthesized as described in Synthesis A. While hot, the sample is divided into five 1 mL aliquots, which receive 10 μL, 20 μL, 50 μL, 100 μL, or 200 μL of PPG-14 butyl ether. Each mixture is vortexed for 5 minutes. In all samples, PPG-14 butyl ether appeared to be immiscible with the DES, and the mixture separated with PPG-14 butyl ether on the top layer. Additional heating to 120° C. for 15 minutes removed the PPG-14 layer, but caused the formation of an emulsion with the PPG-14 butyl ether visibly dispersed in the DES as small bubbles. After cooling to room temperature and sitting undisturbed for 2 days, all samples transformed into opaque white solids.

Synthesis C: Use of Ethanol as a Stabilizing Agent for Trimethylglycine/Urea

A trimethylglycine/urea DES is synthesized as described in Synthesis A. While hot, the sample was divided in three 1 mL aliquots, which received 50 μL, 100 μL, or 150 μL of reagent grade ethanol. After vortexing, all samples appeared as clear solutions, which were left undisturbed for 2 days. After 2 days, only the sample containing 0.05 μL, ethanol remained a liquid. After 4 days, all samples had transformed into opaque white solids.

Synthesis D: Use of NaCl as a Stabilizing Agent for Trimethylglycine/Urea

Three identical syntheses are performed according to Synthesis A. The three samples contained 0.05 mol (5.8551 g) anhydrous trimethylglycine, 0.1 mol urea (6.0052 g), and either 0.01 mol (0.5844 g) NaCl, 0.005 mol (0.2922 g) NaCl, or 0.0025 mol (0.1461 g) NaCl. The mixtures are heated to 125° C. for 1 hour. After heating, all mixtures became clear liquids. The solutions containing 0.01 mol NaCl and 0.005 mol NaCl contained small single crystals, which could be visually identified as NaCl. The DES sample containing 0.0025 mol NaCl was free of precipitate. Upon cooling to room temperature, all NaCl samples remained a liquid for about 12 days before forming opaque white solids.

*It should be noted that the lactic acid used in the following experiments contain 15% water.

For Synthesis E to Synthesis G, carrier systems are prepared using a combination hydrogen bond donors. Starting with the 2:1 molar ratio of urea to trimethylglycine from the above examples, 1 mole of urea is replaced with lactic acid, glycolic acid, or glycerin.

Synthesis E: Synthesis of a Trimethylglycine/Urea DES with Lactic Acid

To a clean 20 mL scintillation vial, added 0.05 mol (5.8551 g) anhydrous trimethylglycine, 0.05 mol (3.0036 g) urea, 0.0025 mol (0.1461 g) NaCl, and 0.05 mol (5.0558 g) lactic acid. The mixture is heated to 90° C. for 3 hours. A yellow liquid was formed. Upon cooling to room temperature, the pH was measured as 5.15. The liquid did not solidify.

Synthesis F: Synthesis of a Trimethylglycine/Urea DES with Glycolic Acid

To a clean 20 mL scintillation vial is added 0.05 mol (5.8551 g) anhydrous trimethylglycine, 0.05 mol (3.0036 g) urea, 0.0025 mol (0.1461 g) NaCl, and 0.05 mol (3.8030 g) glycolic acid. The mixture is heated to 90° C. for 3 hours. A pale yellow liquid was formed. Upon cooling to room temperature, the pH was measured as 5.70. After resting for 10 days, the solution solidified.

Synthesis G: Synthesis of a Trimethylglycine/Urea DES with Glycerin

To a clean 20 mL scintillation vial is added 0.05 mol (5.8551 g) anhydrous trimethylglycine, 0.05 mol (3.0036 g) urea, 0.0025 mol (0.1461 g) NaCl, and 0.05 mol (4.6045 g) glycerin. Because of the consistency of glycerin, the mixture requires manual grinding and additional vortexing to achieve homogeneity before heating. The mixture is heated to 90° C. for 3 hours. A clear liquid was formed with NaCl crystals visible on the bottom of the vial. Upon cooling to room temperature, the pH was measured as 6.30. The solution did not solidify upon cooling.

Synthesis H: Trimethylglycine/Urea DES as a Carrier System for $AlCl_3.6H_2O$

Four identical mixtures are prepared in which 0.0025 mol (0.1461 g) NaCl, 0.05 mol (5.8551 g) anhydrous trimethylglycine, 0.1 mol (6.0022 g) urea are combined with either 1% (0.13295 g), 10% (1.3295 g), 18% (2.6334 g), or 23% (3.6216 g) $AlCl_3.6H_2O$. The mixtures were heated to 100° C. for 3 hours. After the first hour, a clear liquid formed followed by 1 hour of vigorous bubbling, and 1 hour of attenuated bubbling. Upon cooling to room temperature, the solutions containing 10% and 18% $AlCl_3.6H_2O$ remained clear liquids, while the 23% sample formed an opaque white solid. It is theorized that 23% is above the saturation point. The SEC profiles of all three samples indicate peak 4 and peak 5 aluminum species. It can be seen that higher $AlCl_3.6H_2O$ concentrations appear to facilitate the transfer of peak 5 to peak 4 species, when heating time and temperature are kept constant.

| Area (mV · min) | Weight % $AlCl_3 \cdot 6H_2O$ | | |
| --- | --- | --- | --- |
| | 10 | 18 | 23 |
| Peak 4 | 3.05 | 20.82 | 36.34 |
| Peak 5 | 27.22 | 26.83 | 13.04 |
| Total Area | 30.27 | 47.65 | 49.38 |
| pH | 5.95 | 5.69 | 5.55 |

Synthesis I: Lactic Acid Modified DES as a Carrier System for $AlCl_3.6H_2O$

To a clean 20 mL scintillation vial is added 0.05 mol (5.8551 g) anhydrous trimethylglycine, 0.05 mol (3.0036 g) urea, 0.0025 mol (0.1461 g) NaCl, 0.05 mol (5.0558 g) lactic acid, and 15% (2.4138 g) $AlCl_3.6H_2O$. The mixture is heated to 90° C. for 3 hours. A yellow liquid was formed. During the heating, sparse bubbles evolved. Upon cooling to room temperature and resting, the liquid did not solidify. The SEC profile indicated a single peak appearing at the retention time of peak 5. The pH was 5.66.

Synthesis J: Glycolic Acid Modified DES as a Carrier System for $AlCl_3.6H_2O$

To a clean 20 mL scintillation vial is added 0.05 mol (5.8551 g) anhydrous trimethylglycine, 0.05 mol (3.0036 g) urea, 0.0025 mol (0.1461 g) NaCl, 0.05 mol (3.8067 g) glycolic acid, and 15% (2.2589 g) $AlCl_3.6H_2O$. The mixture is heated at 90° C. for 3 hours. A yellow liquid was formed. During the heating, sparse bubbles were evolved. Upon cooling to room temperature and resting, the liquid did not solidify. The SEC profile indicated a single peak appearing at the peak 5 aluminum species retention time. The pH was 5.47.

Synthesis K: Glycerin Modified DES as a Carrier System for $AlCl_3.6H_2O$

To a clean 20 mL scintillation vial is added 0.05 mol (5.8551 g) anhydrous trimethylglycine, 0.05 mol (3.0036 g) urea, 0.0025 mol (0.1461 g) NaCl, 0.05 mol (4.6045 g) glycerin, and 15% (2.3996 g) $AlCl_3.6H_2O$. The mixture is heated to 90° C. for 3 hours. A clear liquid was formed. After 1 hour of heating, vigorous bubbling were observed. Upon cooling to room temperature and resting, the liquid did not solidify. The SEC indicated two peaks appearing at the retention times of peak 4 and peak 5. The pH was 5.45.

The SEC profiles for Syntheses I, J, and K were measured. The results are shown in the table below. The table indicates that both acid-modified Deep Eutectic-AP systems exclusively contain peak 5 species, which is in contrast to the glycerin-modified Deep Eutectic-AP system in which peak 4 species were formed. The acid-modified systems exhibited minimal amounts of bubbling while unmodified, and the glycerin-modified solutions bubbled vigorously. It is theorized that bubbling is caused by the decomposition of urea into $CO_2$ and $NH_3$. The $NH_3$, in turn, acts as a basic source that promotes aluminum aggregation and peak 4 formation. All systems show comparable total peak areas and thus exhibit similar abilities to dissolve $AlCl_3.6H_2O$.

| Area (mV · min) | I (lactic acid) | J (glycolic acid) | K (glycerin) |
| --- | --- | --- | --- |
| Peak 4 | 0 | 0 | 17.70 |
| Peak 5 | 38.41 | 58.17 | 37.63 |
| pH | 5.66 | 5.47 | 5.45 |

Synthesis L: Trimethylglycine/Urea DES as a Carrier System for Anhydrous $AlCl_3$ To a clean 20 mL scintillation vial is added 0.0025 mol (0.1461 g) NaCl, 0.05 mol (5.8551 g) anhydrous trimethylglycine, 0.1 mol (6.0022 g) urea, and 10% (1.3438 g) anhydrous $AlCl_3$. The mixture is heated to 90° C. for 4 hours. Although a liquid formed, no bubbling occurred and large particles of solid $AlCl_3$ could be observed. The sample was heated additionally to 100° C. for 2 days. There was no change in appearance. Upon cooling to room temperature, the liquid formed a clear gel with suspended white particulate. The SEC could not detect any aluminum species in solution.

Synthesis M: Trimethylglycine/Urea DES as a Carrier System for ACH (Reach™ 103)

To a clean 20 mL scintillation vial is added 0.0025 mol (0.1461 g) NaCl, 0.05 mol (5.8551 g) anhydrous trimethylglycine, 0.1 mol (6.0022 g) urea, and 10% (1.3231 g) aluminum chlorohydrate (Reach™ 103). The mixture is heated to 90° C. for 3 hours. An opaque liquid with solid white precipitate at the bottom of the vial was formed. The solution was heated to 100° C. for two additional days. There was no change in appearance. Upon cooling to room temperature, an opaque white solid formed. The SEC did not detect any aluminum species in solution.

Synthesis N:

10 g aluminum chlorohydrate (Reach™ 103) and 15 g demineralized water were combined in a 250 mL high density polyethylene (HDPE) plastic container. The mixture was shaken until a clear solution was obtained. To this solution was added 100 g glycerin in order to match the viscosity of the ALAS samples. This formed a 8 weight % ACH mixture. Again, the mixture was shaken until a homogenous solution was formed. The pH was measured as 3.05.

Synthesis O:

0.7 g NaCl, 43.4 g anhydrous trimethylglycine, 42 g urea, and 18.9 g $AlCl_3.6H_2O$ were combined and stirred using a vortex dry mixer or overhead stirrer to achieve a rough heterogeneous mixture. The mixture was heated in a glass vessel to 100° C. for 2.5 hours, and the walls of the reaction vessel were scraped at periodic intervals to ensure all starting materials were reacted. After the reaction was complete, the solution was transferred to an HDPE plastic container. The pH was measured as 5.69.

Synthesis P:

0.7 g NaCl, 40.6 g anhydrous trimethylglycine, 33.6 g urea, 10.4 g glycolic acid, and 18.7 g $AlCl_3.6H_2O$ were combined and stirred using a vortex dry mixer or overhead stirrer to achieve a rough heterogeneous mixture. The mixture was heated in a glass vessel to 100° C. for 2.5 hours, and the walls of the reaction vessel were scraped at periodic intervals to ensure all starting materials were reacted. After the reaction was complete, the solution was transferred to an HDPE plastic container. The pH was measured as 4.96.

Synthesis Q:

0.8 g NaCl, 41 g anhydrous trimethylglycine, 27.65 g urea, 22.4 g glycerin, and 20.15 g $AlCl_3.6H_2O$ were combined and stirred using a vortex dry mixer and/or overhead stirrer to achieve a rough heterogeneous mixture. The mixture was heated in a glass vessel to 100° C. for 2.5 hours, and the walls of the reaction vessel were scraped at periodic intervals to ensure all starting materials enter solution. After the reaction was complete, the solution was transferred to a HDPE plastic container. The pH was measured as 5.30.

The SEC profiles for Synthesis N to Synthesis Q were measured and compared. Each was designed to have 2 weight % aluminum

| Synthesis | Description | SEC Peak % | | | Al % | pH |
|---|---|---|---|---|---|---|
| | | Peak 3 | Peak 4 | Peak 5 | | |
| N | 8 weight % ACH in glycerin/water | 51 | 45 | 4 | 2 | 3.05 |
| O | 18% $AlCl_3.6H_2O$ in trimethyl-glycine/urea/NaCl | 0 | 45 | 55 | 2 | 5.69 |
| P | $AlCl_3.6H_2O$ in glycolic acid modified deep eutectic solvent | 0 | 0 | 100 | 2 | 4.96 |
| Q | $AlCl_3.6H_2O$ in deep eutectic solvent modified by 20 weight % glycerin | 0 | 33 | 67 | 2 | 5.30 |

The aluminum chlorohydrate control, N, is the only sample that contains peak 3 species. Previous light scattering studies have indicated that aluminum species eluting in peak 3 have molecular weights approximately 3 times larger than species eluting in peak 4. This finding is correlated with the results of previous clinical studies demonstrating that the efficacy of peak 3 aluminum species is significantly lower than peak 4 species. Synthesis P is entirely comprised of peak 5 aluminum species. Peak 5 is known to contain monomeric and the smallest of the oligomeric aluminum species, and it has been determined by light scattering to have molecular weights approximately 4 times smaller than peak 4. Aqueous aluminum chloride, contains only peak 5 species. Lastly, Syntheses O and Q exhibit similar elution profiles.

The samples from Synthesis N to Synthesis Q were aged for 120 days at 28° C. For Synthesis O to Synthesis Q, there was no significant change to the SEC profile, which demonstrates that the antiperspirant actives do no interact with deep eutectic solvent systems. For the aluminum chlorohydrate control, peak 4 increased after aging. Previous aging studies have indicated that the exact nature of hydrolysis in aqueous ACH solutions is dependant upon the concentration. Above 10% ACH, peak 3 is found to increase upon aging. Below 10% ACH, peak 4 is found to increase upon aging. In either situation, the active aluminum species are prone to react with the solvent system, altering the intended distribution of active species.

Synthesis R: Trimethylglycine/Urea DE as a Solvent System for $AlCl_3.6H_2O$ without NaCl To a clean 20 mL scintillation vial is added 0.05 mol (5.8551 g) anhydrous trimethylglycine, 0.1 mol (6.0052 g) urea, and 18 weight % (2.6334 g) $AlCl_3.6H_2O$. The mixture is vortexed and heated to 100° C. for 3 hours. After about 1 hour, a clear liquid formed followed by 1 hour of vigorous bubbling, and 1 hour of attenuated bubbling. Upon cooling to room temperature, the liquid remained. Aging of the bulk sample at room temperature for 1 week resulted in the formation of a white opaque solid.

An aliquot of the material from Synthesis R (18 weight % $AlCl_3.6H_2O$ without NaCl) and a sample with 18 weight % $AlCl_3.6H_2O$ with 1 weight % NaCl were cooled to below 0° C. and allowed to return to room temperature. Both samples remained liquid at low temperatures, forming clear, glass-like phases. The sample without the NaCl solidified upon returning to room temperature, while the NaCl containing sample remained stable indefinitely.

A comparison was made between the material from Synthesis R (18 weight % $AlCl_3.6H_2O$ without NaCl) to a composition of 18 weight % $AlCl_3.6H_2O$ with 1 weight % NaCl. The SEC profiles are given in the table below.

| Area (mV · min) | 18 weight % $AlCl_3.6H_2O$ | 18 weight % $AlCl_3.6H_2O$ with 1 weight % NaCl |
|---|---|---|
| Peak 4 | 13.26 | 20.82 |
| Peak 5 | 35.70 | 26.83 |
| Peak5/Peak 4 | 2.69 | 1.29 |
| Total Area | 48.96 | 47.65 |

Synthesis S:

0.0055 mol (1.3295 g) $AlCl_3.6H_2O$, 0.05 mol (5.8546 g) anhydrous trimethylglycine, 0.1 mol (6.022 g) urea, and 0.0025 mol (0.1336 g) NaCl are added to a clean and dry 20 mL scintillation vial. The weight of $AlCl_3.6H_2O$ is about 10% of the total weight. The vial is vortexed for 10 seconds to achieve a rough heterogeneous powder mixture. The vial is placed in 120° C. oven for 1 hour. The vial is vortexed again for 1 minute. The vial is placed in a 120° C. oven for another hour before taking it out of the oven and allowing it to cool to room temperature. The pH of this solution was 6.3.

Comparison of anhydrous liquid antiperspirant compositions to antiperspirants in water. A 10 weight % aluminum chlorohydrate (Reach™ 103) is prepared by mixing aluminum chlorohydrate in water to form a 10 weight % mixture. The 7.38 weight % $AlCl_3$ is prepared by mixing $AlCl_3$ in a 0.05 mol anhydrous trimethylglycine, 0.1 mol urea, and 0.0025 mol NaCl mixture. A 1 weight % anhydrous aluminum chloride is prepared by mixing aluminum chloride in water to fours a 1 weight % mixture. The 0.76 weight % $AlCl_3$ is prepared by mixing the $AlCl_3$ in a 0.05 mol anhydrous trimethylglycine, 0.1 mol urea, and 0.0025 mo1 ethanol mixture. The samples were analyzed by SEC. The results are in the table below.

| Sample Name | Peak 3 | Peak 4 | Peak 5 | Peak(4/3) |
|---|---|---|---|---|
| 10% ACH in $H_2O$ | 59.7 | 39.04 | 1.26 | 0.65 |
| 7.38% $AlCl_3$ in trimethylglycine/urea/NaCl | 9.79 | 88.83 | 1.38 | 9.07 |
| 1% $AlCl_3$ in $H_2O$ | N/A | N/A | 164368 | N/A |
| 0.76% $AlCl_3$ in trimethylglycine/urea/ethanol | N/A | N/A | 126230 | N/A |

The following examples use the following anhydrous liquid antiperspirant composition for which different skin-feel additives are added, 0.2 g for each additive. The formula is a "solution" of 18% $AlCl_3.6H_2O$ in a typical 2:1 trimethylglycine:urea DES. However, a small amount NaCl (1-2%) is added to aid in melting the solids and preventing the ALAS from solidifying at room temperature. Also, the trimethylglycine:urea ratio is slightly modified (2.065 vs. 1.950) to keep Urea content as low as possible. The ingredients are combined together as solids and then heated at 100° C. for about 4 hours with occasional stirring. This formulation is colorless and odorless with a viscosity that increases substantially upon cooling.

In the examples below, the amounts for the materials are based on the as supplied amount.

Test Formulations with Skin-Feel Additives

The following compositions are made by mixing of the ingredients in the anhydrous liquid.

Formulation Properties:

All properties are ranked on a scale of 1-5. For instance, when rating tackiness, 1 is little tack (like water), 3 is moderate tack (like honey), and 5 is excessive tack (like glue). This follows for each property rated. Initial properties refer to the property of the formula after immediate delivery to the skin (no rubbing or spreading). Final properties refer to when the delivered amount has been fully applied (by rubbing or spreading). For viscosity, a rating of 1 is similar to vegetable oil and a rating of 5 is similar to honey. For sheen 1 is matte, 3 is satin, and 5 is gloss. Drag: 1 is high drag meaning that the sample does not spread easily on the skin. It must be rubbed vigorously (imagine spreading peanut butter). 3 is medium drag like spreading petroleum jelly. It can be spread with fingertips with moderate effort. 5 is little drag and high spreadability like typical moisturizing lotions (imagine spreading lotion on the hand). It can be done with fingertips with little effort. Adhesion: in this case adhesion is contrasted to beading, that is 1 equates to good skin adhesion (when the sample is applied it evenly coats the area and does not separate and bead). 3 equates to moderate adhesion with potential separation—the sample has to be rubbed with effort to coat the area with an even layer. 5 equates to poor adhesion and sample beading—after being spread the sample pools and beads like water on a waxed surface. Warming/Cooling: here warming and cooling are contrasted with 1 indicating a warming sensation, 3 being neutral, and 5 being a cooling sensation like water or alcohol evaporating from the skin (like hand sanitizer gel). Oiliness: 1 is no oily or greasy feeling (like rubbing bare skin or rubbing water on skin). 3 is moderate oily feeling like rubbing sunscreen or typical moisturizing lotion on skin. 5 is very oily or greasy feeling like rubbing cooking oil on skin.

TF1: Formula is semi-translucent with a texture and appearance like petroleum jelly and a viscosity similar to honey. Any opacity is lost after application when formula is warmed by skin and then spread.

| Formula ID | Description |
|---|---|
| TF1 | anhydrous liquid antiperspirant composition (94 weight %) Isopropanol (3.5 weight %) CAPB (1.5 weight %) DI (1.0 weight %) |
| TF2 | anhydrous liquid antiperspirant composition (88.25 weight %) Isopropanol (10 weight %) CAPB (1.25 weight %) DC5329 (0.5 weight %) |
| TF3 | anhydrous liquid antiperspirant composition (91.95 weight %) Isopropanol (3.9 weight %) Steareth-20 (2.06 weight %) Steareth-2 (1.54 weight %) DC345 (0.55 weight %) |
| TF4 | anhydrous liquid antiperspirant composition (80 weight %) Ethanol (18-19 weight %) CAPB (1-2 weight %) |
| TF5 | anhydrous liquid antiperspirant composition (99.5 weight %) DC5329 (0.5 weight %) |
| TF6 | anhydrous liquid antiperspirant composition (100 weight %) |
| TF7 | anhydrous liquid antiperspirant composition (95 weight %) DI (4.95 weight %) Polyox (0.05 weight %) - hot mix |
| TF8 | anhydrous liquid antiperspirant composition (98 weight %) $H_2O$ (2 weight %) |
| TF9 | anhydrous liquid antiperspirant composition (98 weight %) 0.05 weight % Polyox (2 weight %) - cold mix |
| TF10 | anhydrous liquid antiperspirant composition-24* (85.3 weight %) Isopropanol (9.6 weight %) cocamidopropyl trimethylglycine (2.1 weight %) DC5329 (1.5 weight %) DC345 (1.5 weight %) |
| TF11 | anhydrous liquid antiperspirant composition-24 (90.2 weight %) Ethanol (6.8 weight %) cocamidopropyl trimethylglycine (3 weight %) |
| TF12 | anhydrous liquid antiperspirant composition (86 weight %) DC5329 (4 weight %) Isopropanol (5.5 weight %) 0.025 weight % Polyox (2.25 weight %) DC345 (2.25 weight %) |

*anhydrous liquid antiperspirant composition-24 is an anhydrous liquid antiperspirant composition that has been baked for 24 hours - more viscous

| TF1 | Initial | Final |
|---|---|---|
| Viscosity | 4 | 2 |
| Tack | 3 | 1 |
| Drag/Spreadability (1/5) | 2 | 4 |
| Adhesion/Beading (1/5) | 4 | 1 |
| Warming/Cooling (1/5) | 2 | 3 |
| Oiliness | 3 | 4 |
| Sheen | 5 | 3 |

TF2: Formula is mostly translucent with an appearance and viscosity similar to cloudy corn syrup. It has a smooth texture and viscosity reduces dramatically upon warming.

| TF2 | Initial | Final |
|---|---|---|
| Viscosity | 3 | 2 |
| Tack | 2 | 1 |
| Drag/Spreadability (1/5) | 3 | 4 |
| Adhesion/Beading (1/5) | 3 | 1 |
| Warming/Cooling (1/5) | 2 | 2 |
| Oilyness | 3 | 3 |
| Sheen | 5 | 3 |

TF3: Formula is opaque white with a texture and appearance similar to petroleum jelly and a viscosity similar to honey. Opacity is lost after warming and spreading. Waxy emulsifiers increase tack and drag.

| TF3 | Initial | Final |
|---|---|---|
| Viscosity | 5 | 3 |
| Tack | 4 | 2 |
| Drag/Spreadability (1/5) | 2 | 3 |
| Adhesion/Beading (1/5) | 2 | 1 |
| Warming/Cooling (1/5) | 3 | 3 |
| Oilyness | 3 | 2 |
| Sheen | 3 | 3 |

TF4: Formula is crystal clear with an appearance and viscosity similar to baby oil. It is the only formulation below 85 weight % anhydrous liquid antiperspirant composition.

| TF4 | Initial | Final |
|---|---|---|
| Viscosity | 1 | 1 |
| Tack | 1 | 1 |
| Drag/Spreadability (1/5) | 5 | 4 |
| Adhesion/Beading (1/5) | 1 | 1 |
| Warming/Cooling (1/5) | 4 | 3 |
| Oilyness | 2 | 2 |
| Sheen | 4 | 3 |

TF5: Formula is semi-opaque with the consistency of honey. Opacity lost when warmed. Minimal additives—0.05 weight % DC5329, 99.5 weight % anhydrous liquid antiperspirant composition.

| TF5 | Initial | Final |
|---|---|---|
| Viscosity | 4 | 2 |
| Tack | 4 | 4 |
| Drag/Spreadability (1/5) | 2 | 3 |
| Adhesion/Beading (1/5) | 4 | 4 |
| Warming/Cooling (1/5) | 3 | 3 |
| Oilyness | 4 | 4 |
| Sheen | 4 | 4 |

TF6: Original 100 weight % anhydrous liquid antiperspirant composition.

| TF6 | Initial | Final |
|---|---|---|
| Viscosity | 4 | 2 |
| Tack | 4 | 2 |
| Drag/Spreadability (1/5) | 2 | 3 |
| Adhesion/Beading (1/5) | 5 | 4 |
| Warming/Cooling (1/5) | 2 | 2 |
| Oilyness | 3 | 4 |
| Sheen | 5 | 4 |

TF7: Formula is clear with a viscosity like vegetable oil. The water content is high, around 5 weight %. This was the first formula with Polyox that was first hydrated with water and then baked with the solid precursors.

| TF7 | Initial | Final |
|---|---|---|
| Viscosity | 1 | 2 |
| Tack | 1 | 2 |
| Drag/Spreadability (1/5) | 5 | 4 |
| Adhesion/Beading (1/5) | 5 | 3 |
| Warming/Cooling (1/5) | 4 | 4 |
| Oilyness | 4 | 4 |
| Sheen | 5 | 4 |

TF8: Formula is clear with a viscosity like honey.

| TF8 | Initial | Final |
|---|---|---|
| Viscosity | 4 | 3 |
| Tack | 4 | 4 |
| Drag/Spreadability (1/5) | 1 | 2 |
| Adhesion/Beading (1/5) | 5 | 4 |
| Warming/Cooling (1/5) | 2 | 3 |
| Oilyness | 4 | 3 |
| Sheen | 5 | 4 |

TF9: Similar TF7, the formulation differs in that that polyox solution was incorporated after the anhydrous liquid antiperspirant composition was formed. This way the amount of water could be kept under 2 weight %.

| TF9 | Initial | Final |
|---|---|---|
| Viscosity | 4 | 2 |
| Tack | 1 | 2 |
| Drag/Spreadability (1/5) | 5 | 4 |
| Adhesion/Beading (1/5) | 5 | 3 |
| Warming/Cooling (1/5) | 4 | 4 |
| Oilyness | 4 | 4 |
| Sheen | 5 | 4 |

TF10: Formula made with anhydrous liquid antiperspirant composition-24 which is more viscous than anhydrous liquid antiperspirant composition that has only been baked for the standard 4 hours. The consistency is almost that of a soft wax, but it melts and loses it opacity upon warming.

| TF10 | Initial | Final |
|---|---|---|
| Viscosity | 5 | 2 |
| Tack | 5 | 2 |
| Drag/Spreadability (1/5) | 1 | 4 |
| Adhesion/Beading (1/5) | 1 | 1 |
| Warming/Cooling (1/5) | 3 | 3 |

-continued

| TF10 | Initial | Final |
| --- | --- | --- |
| Oilyness | 3 | 4 |
| Sheen | 4 | 4 |

TF11: Formula made with anhydrous liquid antiperspirant composition-24 and ethanol is clear but highly viscous and glassy. Like the other anhydrous liquid antiperspirant composition-24 formulation, there is almost no beading.

| TF11 | Initial | Final |
| --- | --- | --- |
| Viscosity | 5 | 2 |
| Tack | 4 | 1 |
| Drag/Spreadability (1/5) | 1 | 4 |
| Adhesion/Beading (1/5) | 1 | 1 |
| Warming/Cooling (1/5) | 3 | 3 |
| Oilyness | 2 | 4 |
| Sheen | 5 | 4 |

TF12: Formulation is opaque white and creamy. It was made with a new batch of anhydrous liquid antiperspirant composition that was baked for 4 hours at 100° C. and turned out to be more viscous than normal. The formula is still less viscous than those made with the anhydrous liquid antiperspirant composition-24.

| TF12 | Initial | Final |
| --- | --- | --- |
| Viscosity | 4 | 2 |
| Tack | 3 | 2 |
| Drag/Spreadability (1/5) | 2 | 4 |
| Adhesion/Beading (1/5) | 1 | 1 |
| Warming/Cooling (1/5) | 3 | 3 |
| Oilyness | 3 | 4 |
| Sheen | 3 | 4 |

What is claimed is:

1. An anhydrous liquid antiperspirant composition comprising:
   a) a carrier comprising trimethylglycine, urea, and at least one stabilizing agent, wherein the amount of carrier is greater than the amount of any other material in the composition, wherein the carrier is in the form of a deep eutectic solvent, and
   b) an antiperspirant active.

2. The anhydrous liquid antiperspirant composition of claim 1, wherein the molar ratio of trimethylglycine to urea is 1:2.

3. The anhydrous liquid antiperspirant composition of claim 1, wherein the composition comprises greater than 50 weight% of the carrier.

4. The anhydrous liquid antiperspirant composition of claim 1, wherein the antiperspirant active comprises $AlCl_3 \cdot 6H_2O$.

5. The anhydrous liquid antiperspirant composition of claim 1, wherein the composition comprises 5 to 25 weight % of the antiperspirant active.

6. The anhydrous liquid antiperspirant composition of claim 1, wherein the antiperspirant active comprises $AlCl_3 \cdot 6H_2O$.

7. The anhydrous liquid antiperspirant composition of claim 1, wherein the stabilizing agent is at least one stabilizing agent chosen from chloride salts, sodium chloride, potassium chloride, bromides, nitrates, organic acids, glycerin, alcohol, ethanol, and isopropanol.

8. The anhydrous liquid antiperspirant composition of claim 1, wherein the stabilizing agent comprises sodium chloride.

9. The anhydrous liquid antiperspirant composition of claim 1, wherein the composition comprises 1 to 20 weight % of the stabilizing agent.

10. The anhydrous liquid antiperspirant composition of claim 1, further comprising at least one additional hydrogen bond donor.

11. The anhydrous liquid antiperspirant composition of claim 10, wherein the urea and the additional hydrogen bond donor are present in a 1:1 ratio.

12. The anhydrous liquid antiperspirant composition of claim 1 further comprising a skin-feel additive.

13. The anhydrous liquid antiperspirant composition of claim 12, wherein the skin-feel additive is at least one skin-feel additive chosen from water, isopropanol, ethanol, cocamidopropyl trimethylglycine, cyclomethicone, PEG-12 dimethicone copolyol, steareth-2/steareth-20, polyoxyethylene homopolymer, palm kernel oil, mineral oil, and silicone polyether wax, wherein a total amount of free water in the composition is 5 weight % or less.

14. The anhydrous liquid antiperspirant composition of claim 12, wherein the skin-feel additive is present in an amount of 1 to 8 weight %.

15. The anhydrous liquid antiperspirant composition of claim 1, wherein the composition comprises $AlCl_3 \cdot 6H_2O$ and sodium chloride.

16. A method comprising applying the anhydrous liquid antiperspirant composition of claim 1 to an axillary area.

* * * * *